United States Patent [19]

Kosley, Jr. et al.

[11] Patent Number: 5,106,856
[45] Date of Patent: Apr. 21, 1992

[54] [(ARYLALKYLPIPERIDIN-4-YL)METHYL]-2A,3,4,5-TETRAHYDRO-1(2H)-ACENAPHTHYLEN-1-ONES AND RELATED COMPOUNDS

[75] Inventors: Raymond W. Kosley, Jr., Bridgewater; Bettina Spahl, Edison, both of N.J.

[73] Assignee: Hoechst-Roussel Pharmaceuticals Inc., Somerville, N.J.

[21] Appl. No.: 713,249

[22] Filed: Jun. 7, 1991

[51] Int. Cl.$^5$ ............... C07D 211/06; A61K 31/445
[52] U.S. Cl. .................... 514/321; 514/325; 546/197; 546/204
[58] Field of Search ............... 546/197, 204; 514/319, 514/321, 325

[56] References Cited

U.S. PATENT DOCUMENTS 2,589,934  8/1950  Glenn ........................... 546/204
3,391,178  7/1968  Campaigne ................... 546/204

Primary Examiner—C. Warren Ivy
Assistant Examiner—Celia Chang
Attorney, Agent, or Firm—Tatsuya Ikeda

[57] ABSTRACT

There are disclosed various compounds of the formula below,

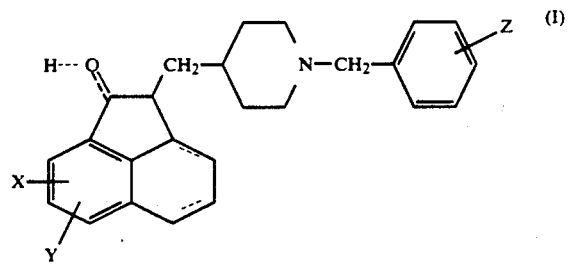

where
X is hydrogen, loweralkyl, loweralkoxy, hydroxy or nitro;
Y is hydrogen or loweralkoxy; or alternatively, X and Y combined together form the group —OCH$_2$O— in which case the positions of X and Y on the benzene ring moiety must be adjacent to each other;
and Z is hydrogen, loweralkyl, loweralkoxy, hydroxy, halogen or nitro;

which compounds are useful for alleviating various memory dysfunctions characterized by a cholinergic deficit such as Alzheimer's disease.

21 Claims, No Drawings

[(ARYLALKYLPIPERIDIN-4-YL)METHYL]-2A,3,4,5-TETRAHYDRO-1(2H)-ACENAPHTHYLEN-1-ONES AND RELATED COMPOUNDS

The present invention relates to compounds having the formula,

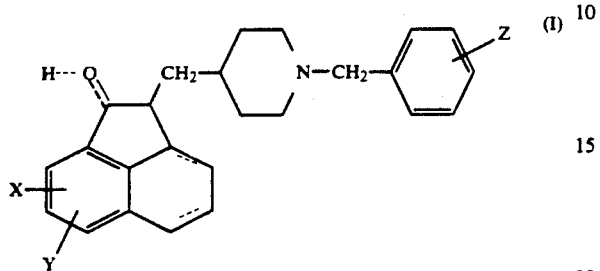

where
- X is hydrogen, loweralkyl, loweralkoxy, hydroxy or nitro;
- Y is hydrogen or loweralkoxy; or alternatively, X and Y combined together form the group —OCH$_2$O— in which case the positions of X and Y on the benzene ring moiety must be adjacent to each other;
- and Z is hydrogen, loweralkyl, loweralkoxy, hydroxy, halogen or nitro;

which compounds are useful for alleviating various memory dysfunctions such as Alzheimer's disease.

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-butyl, sec-butyl and straight- and branched-chain pentyl and hexyl.

The term halogen shall mean fluorine, chlorine, bromine or iodine.

Throughout the specification and the appended claims, a given chemical formula or name shall encompass all stereo and tautomeric isomers where such isomers exist.

Throughout the specification and the appended claims, dotted lines shall mean optional bonds, and wavy lines shall signify geometrical isomers.

The compounds of this invention are prepared by utilizing one or more of the synthetic steps described below.

Throughout the description of the synthetic steps, the notations X, Y and Z shall have the respective meanings given above unless otherwise stated or indicated.

STEP A

A compound of Formula II is allowed to cyclize with the aid of polyphosphoric acid to afford a compound of Formula III. This reaction is typically conducted in an excess amount of polyphosphoric acid at a temperature of 70° to 125° C., preferably at 85° to 100° C.

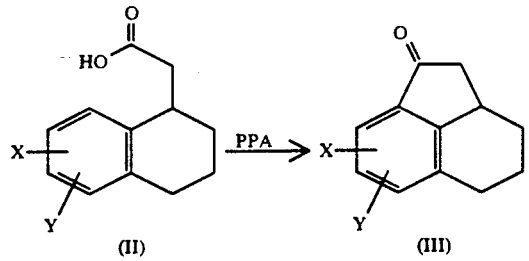

STEP B

Compound III is allowed to react with DDQ (2,3-dichloro-5,6-dicyano-1,4-benzoquinone) to afford a compound of Formula IV. Typically this reaction is conducted in a suitable solvent which allows azeotropic removal of water such as benzene at a temperature of 60° to 90° C., preferably at 75° to 85° C.

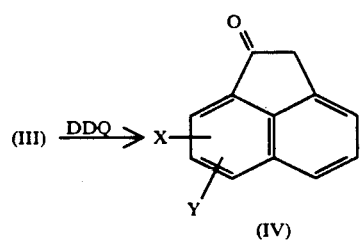

STEP C

A compound of Formula V which is obtained from STEP A or B is allowed to react with LiN[Si(CH$_3$)$_3$]$_2$ at −90° to −40° C., preferably at −78° to −60°, followed by addition of pyridin-4-carboxaldehyde and warming to −20° to +50° C., preferably −10° to +25° C. to afford a compound of Formula VI. This reaction is typically conducted in a suitable solvent such as tetrahydrofuran.

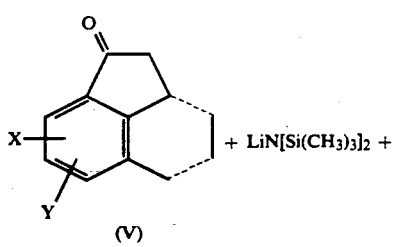

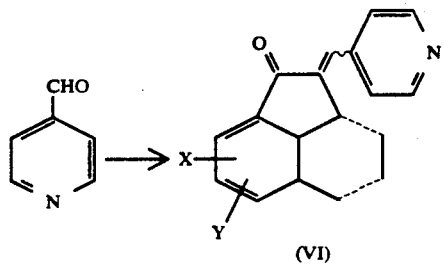

STEP D

Compound VI is hydrogenated at 1 to 50 psi of hydrogen, preferably at 5 to 25 psi of hydrogen with the aid of a suitable catalyst such as platinum oxide to afford a compound of Formula VII. This hydrogenation is typically conducted in a suitable medium such as acetic acid at a temperature of 16° to 50° C., preferably at a temperature of 16° to 35° C.

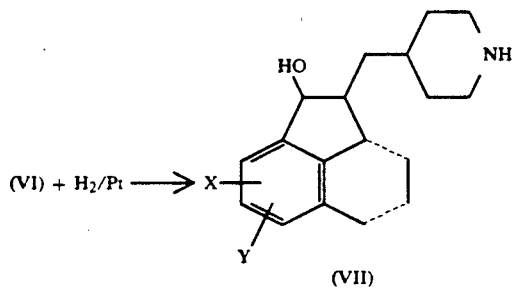

STEP E

Compound VII is allowed to react with a compound of Formula VIII to afford a compound of Formula IX. This reaction is typically conducted with the aid of a suitable base such as potassium carbonate or potassium hydroxide, preferably milled potassium carbonate in a suitable solvent such as 2-butanone at a temperature of 0° to 50° C., preferably 10° to 40° C.

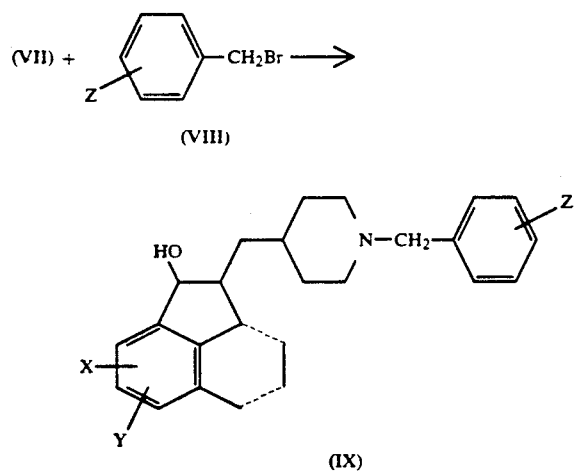

STEP F

Compound IX is allowed to react with a suitable oxidizing agent such as a combination of oxalyl chloride and dimethylsulfoxide to afford a compound of Formula X. This reaction is typically conducted in a suitable solvent such as dichloromethane or dichloromethane/dimethylsulfoxide at a temperature of −80° to −20° C., preferably −70° to −40° C.

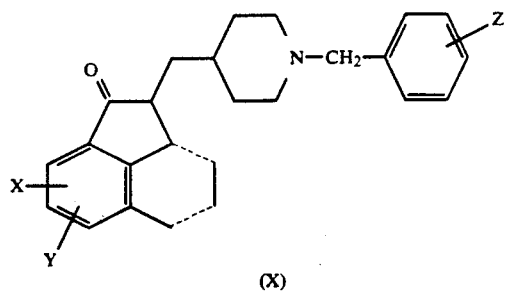

The compounds of Formula I of the present invention are useful for the treatment of various memory dysfunctions such as Alzheimer's disease.

The activity to alleviate such memory dysfunctions is manifested by the ability of these compounds to inhibit the enzyme acetylcholinesterase and thereby increase acetylcholine levels in the brain.

CHOLINESTERASE INHIBITION ASSAY

Cholinesterases are found throughout the body, both in the brain and in serum. However, only brain acetylcholinesterase (AChE) distribution is correlated with central cholinergic innervation. This same innervation is suggested to be weakened in Alzheimer patients. We have determined in vitro inhibition of acetylcholinesterase activity in rat striatum.

IN VITRO INHIBITION OF ACETYLCHOLINESTERASE ACTIVITY IN RAT STRIATUM

Acetylcholinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in brain roughly correlates with cholinergic innervation and subfractionation shows the highest level in nerve terminals.

It is generally accepted that the physiological role of AChE is the rapid hydrolysis and inactivation of acetylcholine. Inhibitors of AChE show marked chlolinomimetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's disease.

The method described below was used in this invention for assaying cholinesterase activity. This is a modification of the method of Ellman et al., Biochem. Pharmacol. 7, 88 (1961).

PROCEDURE

A. Reagents
1. 0.05M Phosphate buffer, pH 7.2
   (a) 6.85 g $NaH_2PO_4 \cdot H_2O$/100 ml distilled $H_2O$
   (b) 13.40 g $Na_2HPO_4 \cdot 7H_2O$/100 ml distilled $H_2O$
   (c) add (a) to (b) until pH reaches 7.2
   (d) Dilute 1:10
2. Substrate in buffer
   (a) 198 mg acetylthiocholine chloride (10 mM)
   (b) q.s. to 100 ml with 0.05M phosphate buffer, pH 7.2 (reagent 1)

3. DTNB in buffer
   (a) 19.8 mg 5,5-dithiobisnitrobenzoic acid (DTNB) (0.5 mM)
   (b) q.s. to 100 ml with 0.05M phosphate buffer, pH 7.2 (reagent 1)
4. A 2 mM stock solution of the test drug is made up in a suitable solvent and q.s. to volume with 0.5 mM DTNB (reagent 3). Drugs are serially diluted (1:10) such that the final concentration (in cuvette) is $10^{-4}$M and screened for activity. If active, IC$_{50}$ values are determined from the inhibitory activity of subsequent concentrations.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2 using a Potter-Elvehjem homogenizer. A 25 microliter aliquot of the homogenate is added to 1.0 milliter vehicle or various concentrations of the test drug and preincubated for 10 minutes at 37° C.

C. Assay

Enzyme activity is measured with the Beckman DU-50 spectrophotometer. This method can be used for IC$_{50}$ determinations and for measuring kinetic constants.

INSTRUMENT SETTINGS

Kinetics Soft-Pac Module #598273 (10)
Program #6 Kindata:
Source—Vis
Wavelength—412 nm
Sipper—none
Cuvettes—2 ml cuvettes using auto 6-sampler
Blank—1 for each substrate concentration
Interval time—15 seconds (15 or 30 seconds for kinetics)
Total time—5 minutes (5 or 10 minutes for kinetics)
Plot—yes
Span—autoscale
Slope—increasing
Results—yes (gives slope)
Factor—1

Reagents are added to the blank and sample cuvettes as follows:

Blank:
0.8 ml Phosphate Buffer/DTNB
0.8 ml Buffer/Substrate

Control:
0.8 ml Phosphate Buffer/DTNB/Enzyme
0.8 ml Phosphate Buffer/Substrate

Drug:
0.8 ml Phosphate Buffer/DTNB/Drug/Enzyme
0.8 ml Phosphate Buffer/Substrate Blank values are determined for each run to control for non-enzymatic hydrolysis of substrate and these values are automatically subtracted by the kindata program available on kinetics soft-pac module. This program also calculates the rate of absorbance change for each cuvette.

For IC$_{50}$ Determinations:

Substrate concentration is 10 mM diluted 1:2 in assay yielding final concentration of 5 mM. DTNB concentration is 0.5 mM yielding 0.25 mM final concentration.

$$\% \text{ Inhibition} = \frac{\text{slope control} - \text{slope drug}}{\text{slope control}} \times 100$$

IC$_{50}$ values are calculated from log-probit analysis.

Results of this assay for some of the compounds of this invention and physostigmine (reference compound) are presented in Table 1.

TABLE 1

| Compound | Inhibitory Concentration, Brain AChE ($\mu$M) |
|---|---|
| 2-[(N-Benzylpiperidin-4-yl)methyl]-2a,3,4,5-tetrahydro-1(2H)-acenaphthylen-1-one hydrochloride | 1.02 |
| 2-[[N-(3-Fluorobenzyl)piperidin-4-yl]methyl]-2a,3,4,5-tetrahydro-1(2H)-acenaphthylen-1-one hydrochloride (Reference Compound) | 4.10 |
| Physostigmine | 0.01 |

This utility is further demonstrated by the ability of these compounds to restore cholinergically deficient memory in the Dark Avoidance Assay described below.

DARK AVOIDANCE ASSAY

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

Results of this assay for some of the compounds of this invention and those for tacrine and pilocarpine (reference compounds) are presented in Table 2.

TABLE 2

| Compound | Dose (mg/kg of body weight, s.c) | % of Animals with Scopolamine Induced Memory Deficit Reversal |
|---|---|---|
| 2-[[N-(3-fluorobenzyl)-piperidin-4-yl]methyl]-2a,3,4,5-tetrahydro-1(2H)-acenaphthylen-1-one hydrochloride | 0.1 | 20 |
| Pilocarpine | 5 | 23 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric 2-naphthalenesulfonic and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvent; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:

2-[(N-Benzylpiperidin-4-yl)methyl]-1,2,2a,3,4,5-hexahydroacenaphthylen-1-ol;

2-[[N-(4-Fluorobenzyl)piperidin-4-yl]methyl]-1,2,2a,3,4,5-hexahydroacenaphthylen-1-ol;

2-[(N-Benzylpiperidin-4-yl)methyl]-2a,3,4,5-tetrahydro-1(2H)-acenaphthylen-1-one;

2-[[N-(3-Fluorobenzyl)piperidin-4-yl]methyl]-1,2,2a,3,4,5-hexahydroacenaphthylen-1-ol;

2-[[N-(3-Fluorobenzyl)piperidin-4-yl]methyl]-2a,3,4,5-tetrahydro-1(2H)-acenaphthylen-1-one;

2-[(N-Benzylpiperidin-4-yl)methyl]-6-methoxy-2a,3,4,5-tetrahydro-1(2H)-acenaphthylen-1-one;

2-[[N-(3-Fluorobenzyl)piperidin-4-yl]methyl]-6-methoxy-2a,3,4,5-tetrahydro-1(2H)-acenaphthylen-1-one;

2-[(N-Benzylpiperidin-4-yl)methyl]-6,7-dimethoxy-2a,3,4,5-tetrahydro-1(2H)-acenaphthylen-1-one;

2-[[N-(3-Fluorobenzyl)piperidin-4-yl]methyl]-6,7-dimethoxy-2a,3,4,5-tetrahydro-1(2H)-acenaphthylen-1-one;

2-[N-(Benzylpiperidin-4-yl)methyl]-6,7-diethoxy-2a,3,4,5-tetrahydro-1(2H)-acenaphthylen-1-one;

2-[(N-Benzylpiperidin-4-yl)methyl]-6,7-dimethoxy-1(2H)-acenaphthylen-1-one;

2-[[N-(3-Nitrobenzyl)piperidin-4-yl]methyl]-2a,3,4,5-tetrahydro-1(2H)-acenaphthylen-1-one; and 2-[(N-Benzylpiperidin-4-yl)methyl]-6,7-methylenedioxy-2a,3,4,5-tetrahydro-1(2H)-acenaphthylen-1-one.

The following examples are presented in order to illustrate the present invention.

EXAMPLE 1

7,8-Dimethoxy-2a,3,4,5-tetrahydro-1(2H)-acenaphthylen-1-one

To a stirred solution of 135 g of polyphosphoric acid at 90° was added 18.9 g of 6,7-dimethoxy-1,2,3,4-tetrahydro-1-naphthalene acetic acid. The mixture was stirred 4 to 5 minutes at 85°–90°, the heat source being removed for the first several minutes following the addition. To the stirred mixture was then added an additional 100 g of polyphosphoric acid at 80° C. The mixture was stirred at 75°–85° for an additional 5 minutes, allowed to cool to 50° and treated with 350 g of ice water. The mixture was stirred for 20 minutes, cooled to 20°–25°, extracted twice with ether, washed successively with water, twice with 5% sodium hydroxide, water, 3% acetic acid, sodium bicarbonate and water. The resulting solution was dried, filtered and concentrated to an oil which crystallized on standing. The material was dissolved in a small volume of ethyl acetate and filtered through flash silica gel, eluting with 15% ethyl acetate/hexanes to provide 12.6 g of 7,8-dimethoxy-2a,3,4,5-tetrahydro-1(2H)-acenaphtheylen-1-one, m.p. 80°–84°.

Analysis: Caculated for $C_{14}H_{16}O_3$: 72.39% C; 6.94% H. Found: 72.57% C; 6.93% H.

EXAMPLE 2

7,8-Dimethoxy-1(2H)-acenaphthylen-1-one

A mixture of 3.0 g of 7,8-dimethoxy-2a,3,4,5-tetrahydro-1(2H)-acenaphthylen-1-one, 3 g of DDC (2,3-dichloro-5,6-dicyano-1,4-benzoquinone) and 24 ml of azeotropically dried benzene was stirred at 75°–85° C. for 45 minutes and allowed to cool to room temperature. To the mixture was added an additional 3 g of DDQ. The mixture was stirred at 75°–85° for 1.25 hours, allowed to cool to room temperature, diluted with benzene, and the solid residue was washed with benzene. The filtrate was flash chromatographed on silica gel, eluting with dichloromethane to provide 1.36 g of 7,8-dimethoxy-1(2H)-acenaphthylen-1-one. The material was further purified by flash chromatography on silica gel eluting with 25% ethyl acetate/hexanes to provide 1.17 g of an analytically pure solid mp 81°–83°.

Analysis: Calculated for $C_{14}H_{12}O_3$: 73.67% C; 5.30% H. Found: 73.64% C; 5.33% H.

EXAMPLE 3 trans-7,8-Dimethoxy-2-[(pyridin-4-yl)methyleneyl]-2a,3,4,5-tetrahydro1(2H)-acenaphthylen-1-one To a solution of 12.1 g of lithium bis(trimethylsilyl)amide in 200 ml of dry THF at −65° to −70° was added dropwise a solution of 16.8 g of 7,8-dimethoxy-2a,3,4,5-tetrahydro-1(2H)-acenaphthylen-1-one in 325 ml of dry THF. The solution was stirred at −70° to −75° for one hour. To the solution was added dropwise a solution of 6.9 ml (7.73 g) of pyridine-4-carboxaldehyde in 300 ml of dry THF. The mixture was stirred 1.5 hour at −70° to −75° and then 4 hours at 0°. The solution was poured into ice water, extracted twice with ethyl acetate and the organic extract was washed successively with water and saturated NaCl, and thereafter dried ($Na_2SO_4$), filtered and concentrated to an oil. Flash chromatography on silica gel, eluting with 60%, 70%, and 100% ethyl acetate/hexanes provided, after evaporation of solvent, 1.8 g of pure trans-7,8-dimethoxy-2-[(pyridin-4-yl)methyleneyl]-2a,3,4,5-tetrahydro-1(2H)-acenaphthylen-1-one in addition to 4.95 g of a trans material contaminated with a small amount of cis compound. Total yield: 6.75 g.

Analysis: Calculated for $C_{20}H_{19}NO_3$: 74.75% C; 5.96% H; 4.36% N. Found: 74.76% C; 5.90% H; 4.34% N.

EXAMPLE 4

2-[(N-Benzylpiperidin-4-yl)methyl]-1,2,2a,3,4,5-hexahydroacenaphthylen-1-ol

A mixture of 4.08 g of 2-[(pyridin-4-yl)methyleneyl]-2a,3,4,5-tetrahydro-1(2H)-acenaphthylen-1-one dissolved in 64 ml of acetic acid and 0.81 g of $PtO_2$ (wetted with acetic acid) was shaken under $H_2$ (10 to 20 psi) at room temperature for 24 hours. The mixture was filtered over celite and the filtrate concentrated under high vacuum. The oil was then dissolved in 120 ml of 2-butanone. To the solution was added 12.0 g of milled KOH, followed by 1.4 ml of benzyl bromide. The reaction mixture was stirred for 0.5 hr at room temperature, then filtered and concentrated. The material was purified by flash chromatography, employing 20% acetone/hexane. The product-containing fractions were combined and concentrated. The residue was recrystallized from cyclohexane and dried at 110° C. for 3 hrs to provide 1.6 g of 2-[(N-benzylpiperidin-4-yl)methyl]-1,2,2a,3,4,5-hexahydro-acenaphthylen-1-ol, m.p. 145–147.

Analysis: Calculated for $C_{25}H_{32}NO$: 83.06% C; 8.64% H; 3.87% N. Found: 82.96% C; 8.63% H; 3.92% N.

EXAMPLE 5

2-[[N-(4-Fluorobenzyl)piperidin-4-yl]methyl]-1,2,2a,3,4,5-hexahydroacenaphthylen-1-ol hydrocholoride monohydrate A mixture of 1.25 g of platinum (IV) oxide, 6.27 g of 2-[(pyridin-4-yl)methyleneyl]-2a,3,4,5-tetrahydro-1(2H)-acenaphthylen-1-one, and 100 ml of acetic acid was shaken under $H_2$ (15 psi) for 24 hrs. The catalyst was removed by filtration and the filtrate concentrated under high vacuum. The residual oil was dissolved in 187 ml of 2-butanone. To the solution was added 17 g of milled potassium carbonate, followed by 2.37 ml of 4-fluorobenzyl bromide. The reaction mixture was stirred at room temperature under $N_2$ for 24 hours. The reaction mixture was filtered, the precipitate washed with 2-butanone, and the filtrate concentrated. The residual oil was purified by HPLC, eluting with 20% acetone/hexane. The product-containing fractions were combined and concentrated. The residue was dissolved in methanol and ethereal HCl added until the solution became acidic. The solvent was removed under vacuum, and the residue was triturated with ether and dried under high vacuum first at room temperature and then at 110° C. for 24 hrs to provide 2.1 g of 2-[[N-(4-fluorobenzyl)piperidin-4-yl]methyl]-1,2,2a,3,4,5-hexahydroacenaphthylen-1-ol hydrochloride monohydrate, m.p. 138–148.

Analysis: Calculated for $C_{25}H_{33}ClFNO_2$: 69.18% C; 7.60% C; 3.23% N. Found: 69.20% C; 7.28% H; 3.23% N.

EXAMPLE 6

2-[(N-Benzylpiperidin-4-yl)methyl]-2a,3,4,5-tetrahydro-1(2H)-acenaphthylen-1-one hydrochloride To a stirred solution of 0.76 ml of oxalyl chloride in 20 ml of DCM (dichloromethane) at −60° to −70° was added dropwise a solution of 1.30 ml of DMSO (dimethylsulfoxide) in 10 ml of DCM. The solution was stirred at −60° to −70° for 4 min. To the solution was added a mixture of 2.78 g of 2-[(N-benzylpiperidin-4-yl)methyl]-1,2,2a,3,4,5-hexahydroacenaphthylen-1-ol in 10 ml of DCM and 8 ml of DMSO. The resulting mixture was stirred for 15 min at −70° to −60°. To the solution was then added 5.6 ml of triethylamine, and thereafter the mixture was stirred 5 min at −70° to −60°, allowed to warm to room temperature, diluted with DCM, washed successively with cold sodium carbonate, water and brine, dried (sodium sulfate) and concentrated to an oil. The oil was dissolved in ether, washed with water and the water wash extracted with ether. The combined ethereal extracts were washed twice with water and brine, dried ($Na_2SO_4$) and concentrated to an oil. The oil was purified by flash chromatography on silica gel eluting with 40% ethyl acetate/hexanes followed by 50% ethyl acetate/hexanes. The pure product-containing fractions were combined and concentrated to provide an oil which was dissolved in ether and precipitated by addition of ethereal hydrogen chloride. Filtration followed by drying at 113° (2 mm) provided 1.72 g of analytically pure 2-[(N-benzylpiperidin-4-yl)-methyl]-2a,3,4,5-tetrahydro-1(2H)-acenaphthylen-1-one hydrochloride. Recrystallization from ethanol provided colorless plates, m.p. 245–251 d.

Analysis: Calculated for $C_{25}H_{30}ClNO$: 75.83% C; 7.64% H; 3.54% N. Found: 76.01% C; 7.54% H; 3.51% N.

EXAMPLE 7

2-[[N-(3-Fluorobenzyl)piperidin-4-yl]methyl]-1,2,2a,3,4,5-tetrahydro-acenaphthylen-1-ol hydrochloride A suspension of 5.03 g of 2-[(pyridin-4-yl)methyleneyl]-2a,3,4,5-tetrahydro-1(2H)-acenaphthylen-1-one, 80 ml of acetic acid and 1.0 g of PtO$_2$ was shaken at 20 psi H$_2$ for 30 min, 20 to 10 psi for 1 h and 10 psi for 12 h. The suspension was filtered and the filtrate concentrated to an oil which was further dried by azeotroping with toluene. The residue was dissolved in 150 ml of 2-butanone to which was added 15 g of milled potassium carbonate followed by 1.9 ml of 95% m-fluorobenzyl bromide. The suspension was stirred for 3 h at room temperature, filtered and washed with 2-butanone. The filtrate was flash chromatographed on silica gel, eluting with 40% ethyl acetate/hexanes, followed by 50% ethyl acetate/hexanes. The pure product-containing fractions were combined and concentrated to provide a white solid (3.22 g). The material was recrystallized from cyclohexane, dried, dissolved in ether and precipitated as a white solid with ethereal HCl. The solid was isolated by filtration and dried at 110° for 1.5 h to provide analytically pure 2-[[N-(3-fluorobenzyl)piperidin-4-yl]methyl]-1,2,2a,3,4,5-hexahydroacenaphthylen-1-ol hydrochloride, m.p. 118°–168°.

Analysis: Calculated for C$_{25}$H$_{31}$ClFNO: 72.19% C; 7.51% H; 3.37% N. Found: 71.98% C; 7.54% H; 3.33% H.

EXAMPLE 8

2-[[N-(3-Fluorobenzyl)piperidin-4-yl]methyl]-2a,3,4,5-tetrahydro-1(2H)-acenaphthylen-1-one hydrochloride To a stirred solution of 0.96 ml of oxalyl chloride in 20 ml of methylene chloride at −50° to −60° C. was added dropwise a solution of 1.63 ml of DMSO and 0.96 ml methylene chloride. The solution was stirred for 4 min, after which was added dropwise a solution of 3.70 g of 2-[[N-(3-fluorobenzyl)piperidin-4-yl)-methyl]-1,2.2a,3,4,5-hexahydroacenaphthylen-1-ol dissolved in 13 ml of methylene chloride and 10 ml of DMSO. The reaction mixture was stirred for an additional 15 min, after which was added 7.10 ml of Et$_3$N. The reaction mixture was stirred for 5 min. The reaction mixture was then poured into a mixture of methylene chloride/Na$_2$CO$_3$, extracted with methylene chloride, washed successively with water and brine, dried with Na$_2$SO$_4$, filtered, and concentrated. The residue was purified by HPLC, eluting with 30% EtOAc/hexane. The product-containing fractions were combined and concentrated. The residue was dissolved in methanol and ethereal HCl added until the solution became acidic. The solvent was removed under vacuum and the residue was triturated with ether and dried under high vacuum at room temperature and then at 110° C. for 2 hours to provide 2.2 g of 2-[[N-(3-fluorobenzyl)piperidin-4-yl]-2a,3,4,5-tetrahydro-1(2H)-acenaphthylen-1-one hydrochloride, m.p. 220–222.

Analysis: Calculated for C$_{25}$H$_{29}$ClFNO: 72.54% C; 7.06% H; 3.38% N. Found: 72.39% C; 7.09% H; 3.36% N.

We claim:

1. A compound having the formula,

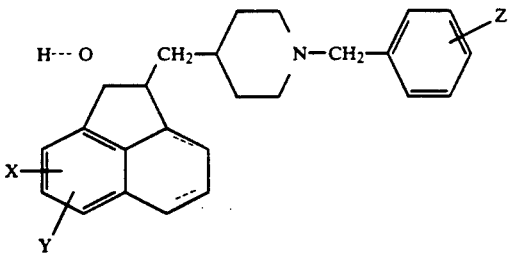

X is hydrogen, loweralkyl, loweralkoxy, hydroxy or nitro; Y is hydrogen or loweralkoxy; or alternatively, X and Y combined together form the group —OCH$_2$O— in which case the positions X and Y on the benzene ring moiety must be adjacent to each other; and Z is hydrogen, loweralkyl, loweralkoxy, hydroxy, halogen or nitro; or a pharmaceutically acceptable acid addition salt thereof.

2. The compound as defined in claim 1, where X is hydrogen, loweralkyl or loweralkoxy.

3. The compound as defined in claim 1, where X is hydrogen or loweralkoxy.

4. The compound as defined in claim 1, where Z is hydrogen, loweralkyl or halogen.

5. The compound as defined in claim 2, where Z is hydrogen, loweralkyl or halogen.

6. The compound as defined in claim 3, where Z is hydrogen, loweralkyl or halogen.

7. The compound as defined in claim 1, which is 2-[(N-benzylpiperidin-4-yl)methyl]-1,2,2a,3,4,5-hexahydroacenaphthylen-1-ol.

8. The compound as defined in claim 1, which is 2-[[N-(4-fluorobenzyl)-piperidin-4-yl]methyl]-1,2,2a,3,4,5-hexahydroacenaphthylen-1-ol.

9. The compound as defined in claim 1, which is 2-[(N-benzylpiperidin-4-yl)methyl]-2a,3,4,5-tetrahydro-1(2H)-acenaphthylen-1-one.

10. The compound as defined in claim 1, which is 2-[[N-(3-fluorobenzyl)-piperidin-4-yl]methyl]-1,2,2a,3,4,5-hexahydroacenaphthylen-1-ol.

11. The compound as defined in claim 1, which is 2-[[N-(3-fluorobenzyl)-piperidin-4-yl]methyl]-2a,3,4,5-tetrahydro-1(2H)-acenaphthylen-1-one hydrochloride.

12. The compound as defined in claim 1, which is 2-[N-(2-benzylpiperidin-4-yl)-methyl]-6-methoxy-2a,3,4,5-tetrahydro-1(2H)-acenaphthylen-1-one.

13. The compound as defined in claim 1, which is 2-[[N-(3-fluorobenzyl)-piperidin-4-yl]methyl]-6-methoxy-2a,3,4,5-tetrahydro-1(2H)-acenaphthylen-1-one.

14. The compound as defined in claim 1, which is 2-[(N-benzylpiperidin-4-yl)-methyl]-6,7-dimethoxy-2a3,4,5-tetrahydro-1(2H)-acenaphthylen-1-one.

15. The compound as defined in claim 1, which is 2-[[N-(3-fluorobenzyl)-piperidin-4-yl]methyl]-6,7-dimethoxy-2a,3,4,5-tetrahydro-1-(2H)-acenaphthylen-1-one.

16. The compound as defined in claim 1, which is 2-[N-(benzylpiperidin-4-yl)-methyl]-6,7-diethoxy-2a,3,4,5-tetrahydro-1(2H)-acenaphthylen-1-one.

17. The compound as defined in claim 1, which is 2-[(N-benzylpiperidin-4-yl)-methyl]-6,7-dimethoxy-1(2H)-acenaphthylen-1-one.

18. The compound as defined in claim 1, which is 2-[[N-(3-nitrobenzyl)-piperidin-4-yl]methyl]-2a,3,4,5-tetrahydro-1(2H)-acenaphthylen-1-one.

19. The compound as defined in claim 1, which is 2-[(N-benzylpiperidin-4-yl)-methyl]-6,7-methylenedioxy-2a,3,4,5-tetrahydro-1(2H)-acenaphthylen-1-one.

20. A pharmaceutical composition comprising a compound as defined in claim 1 in an amount effective for alleviating memory dysfunction, and a suitable carrier therefor.

21. A method of alleviating memory dysfunction which comprises administering to a patient an effective amount of a compound as defined in claim 1.

* * * * *

UNITED STATES PATENT AND TRADEMARK OFFICE
CERTIFICATE OF CORRECTION

PATENT NO. : 5,106,856
DATED : April 21, 1992
INVENTOR(S) : Raymond W. Kosley, Jr. and Bettina Spahl It is certified that error appears in the above-identified patent and that said Letters Patent is hereby corrected as shown below:

In Chemical Formulas V, VI, VII, IX and X appearing in Columns 2, 3 and 4:

Change the dotted line between the 2a and 3-positions of the ring system to optional double bond, namely, "_____".

Column 12, lines 4-5:

Connect the oxygen atom to the 1- position of the ring system with an optional double bond, namely, "_____".

Signed and Sealed this

Twentieth Day of July, 1993

Attest:

MICHAEL K. KIRK

Attesting Officer    Acting Commissioner of Patents and Trademarks